(12) United States Patent
Bartelucci

(10) Patent No.: US 11,071,527 B2
(45) Date of Patent: Jul. 27, 2021

(54) CONTAINER ASSEMBLY

(71) Applicant: MECCANICA G.M. S.R.L., Loreto (IT)

(72) Inventor: Marco Bartelucci, Jesi (IT)

(73) Assignee: MECCANICA G.M. S.R.L., Loreto (IT)

( * ) Notice: Subject to any disclaimer, the term of this patent is extended or adjusted under 35 U.S.C. 154(b) by 289 days.

(21) Appl. No.: 16/097,984

(22) PCT Filed: May 4, 2017

(86) PCT No.: PCT/EP2017/060613
§ 371 (c)(1),
(2) Date: Oct. 31, 2018

(87) PCT Pub. No.: WO2017/191235
PCT Pub. Date: Nov. 9, 2017

(65) Prior Publication Data
US 2019/0142395 A1    May 16, 2019

(30) Foreign Application Priority Data

May 5, 2016  (IT) .................... 102016000046578
Oct. 5, 2016  (IT) .................... 102016000099874

(51) Int. Cl.
*A61B 10/00* (2006.01)
*B01L 3/00* (2006.01)
*G01N 1/31* (2006.01)

(52) U.S. Cl.
CPC .......... *A61B 10/0096* (2013.01); *B01L 3/502* (2013.01); *B01L 3/50853* (2013.01);
(Continued)

(58) Field of Classification Search
CPC ....... A61B 10/0096; B01L 3/50; B01L 3/502; B01L 3/50853; B01L 2300/04;
(Continued)

(56) References Cited

U.S. PATENT DOCUMENTS 5,533,518 A * 7/1996 Vogler .................. B01L 3/5021
600/573
5,817,032 A   10/1998 Williamson, IV et al.
(Continued)

FOREIGN PATENT DOCUMENTS

WO    WO2008152980 A1    8/2010
WO    WO2012171529 A1    12/2012

OTHER PUBLICATIONS

International Search Report and Written Opinion dated Jul. 17, 2017 from counterpart PCT App No. PCT/EP2017/060613.

*Primary Examiner* — Matthew D Krcha
*Assistant Examiner* — Austin Q Le
(74) *Attorney, Agent, or Firm* — Shuttleworth & Ingersoll, PLC; Timothy Klima

(57) ABSTRACT

A container assembly for biopsy including: a container provided with a lower chamber filled with a liquid intended to preserve biopsic samples and an upper chamber, a partition disposed in the upper chamber and provided with a base wall connected to the container; the partition has a lateral wall that raises from the base wall in such a way to define a compartment intended to receive a biopsic sample; disengageable connection means connect the base wall of the partition to the container; a cover is coupled with the container and cooperates with the lateral wall of the partition in such a way to push the partition, to force the disengageable connection means and to cause the disengagement of the base wall of the partition from the container.

13 Claims, 17 Drawing Sheets

(52) U.S. Cl.
CPC .......... *G01N 1/31* (2013.01); *B01L 2300/042* (2013.01); *B01L 2300/047* (2013.01); *B01L 2300/0672* (2013.01); *B01L 2300/0832* (2013.01)

(58) Field of Classification Search
CPC ......... B01L 2300/041; B01L 2300/042; B01L 2300/047; B01L 2300/0672; B01L 2300/0832; G01N 1/31
See application file for complete search history.

(56) References Cited

U.S. PATENT DOCUMENTS

| | | | |
|---|---|---|---|
| 2009/0104692 A1* | 4/2009 | Bartfeld | G01N 1/28 435/325 |
| 2009/0193880 A1* | 8/2009 | Halverson | B01F 15/00837 73/64.56 |
| 2010/0155343 A1* | 6/2010 | Battles | B01D 17/12 210/789 |
| 2012/0196313 A1* | 8/2012 | Williams | B01F 13/002 435/29 |
| 2014/0051178 A1* | 2/2014 | Niggel | A61B 10/0096 436/164 |
| 2015/0037830 A1* | 2/2015 | Jakobsen | G01N 1/28 435/29 |
| 2015/0158027 A1 | 6/2015 | Fleming et al. | |
| 2017/0258683 A1* | 9/2017 | Tsakas | A61K 9/08 |

\* cited by examiner

CONTAINER ASSEMBLY

This application is the National Phase of International Application PCT/EP2017/060613 filed May 4, 2017 which designated the U.S.

This application claims priority to Italian Patent Application No. 102016000046578 filed May 5, 2016 and Italian Patent Application No. 102016000099874 filed Oct. 5, 2016. Both applications are incorporated by reference herein.

TECHNICAL FIELD

The present patent application for industrial invention relates to a container assembly for biopsy.

As it is known, in order to make a biopsy, a histological or biopsic sample is taken from the patient and is delivered to a test center that will carry out the biopsy or histopathologic analysis.

BACKGROUND ART

Containers are known for the transportation of said histological samples, which contain formaldehyde, wherein the sample is immersed in order to be preserved.

However, the exposure to vapors exhaled from formaldehyde involves hazards for the operator's health. As a matter of fact, it has been proved that formaldehyde is carcinogenic and involves a set of secondary effects, such as headache, irritation of eyes, skin, oral cavity and airways, cough, drowsiness, asthenia, memory loss, menstrual irregularities, bronchial asthma, skin irritative lesions.

Various types of container assemblies are known in order to avoid exposing the operator to formaldehyde exhalations.

WO2012171529 describes a container assembly comprising a container for storing a tissue sample and a cover, wherein a preservation liquid is contained, which is fluid-tight sealed with a membrane. A puncturing member is mounted in the cover and can be actuated by the user in order to break the membrane when the cover is closed on the container. In this way the liquid passes through the membrane, going from the cover to the container in order to drown the sample.

Such device of the prior art is impaired by some drawbacks. In fact, it must be noted that the tissue sample is generally sticky and tends to stick to the bottom of the container. Consequently, if the container is overturned, the liquid goes into the cover and the sample that adheres to the bottom of the container is not covered by the liquid. Therefore, such container assemblies must be transported in perfectly vertical position.

A second type of container assembly is known, which comprises a first container intended to contain a tissue sample and a second container containing a preservation liquid. The first and the second container have walls provided with two holes, which face one another. The two containers can move one respect to the other in order to go from a closing position, wherein the holes of the two walls are not in communication and therefore the liquid remains enclosed in the second container, to an opening position, wherein the holes of the two walls are in communication and therefore the liquid can pass from the second container to the first container in order to drown the sample.

Also this type of device of the prior art is impaired by some drawbacks. In fact, it must be considered that the liquid contained in the second container is not perfectly fluid-tight sealed when the container assembly is in closing position. Moreover, the actuation of the two containers is not especially simple for the user because the user must actuate the containers in such a way to center the holes of the walls in order to open the container assembly. Furthermore, the user must remember to close the container assembly in order to prevent the preservation liquid from returning into the second container if the container assembly is overturned.

Containers for biopsy are also known which are filled with formaldehyde and with an oily liquid that forms a surface barrier on the formaldehyde in order to inhibit exhalations. This type of containers is not perfectly safe and reliable.

DISCLOSURE OF THE INVENTION

The purpose of the present invention is to eliminate the drawbacks of the prior art by devising a container assembly for biopsy that is able to preserve a biopsic sample in an efficient and safe way for the user's health.

Another purpose of the present invention is to provide such a container assembly that is practical, reliable and simple to make and use.

These purposes are achieved according to the container of the present disclosure.

Advantageous embodiments appear from the present container. The container assembly for biopsy according to the invention comprises:
 a container provided with a lower chamber that is filled with a liquid intended to preserve biopsic samples and with an upper chamber disposed above the lower chamber,
 a partition disposed in the upper chamber of the container and provided with a base wall connected to the container, in such a way to isolate the lower chamber from the upper chamber.

The partition comprises upper lateral walls that raise from said base wall in such a way to define a compartment intended to receive a biopsic sample.

The container assembly also comprises:
 disengageable connection means that connect the base wall of the partition to the container in a disengageable way; and
 a cover that is coupled with said container and cooperates with said side wall of the partition in such a way to push the partition, force said disengageable connection means and cause the disengagement of the base wall of the partition from the container, in such manner that the partition with the biopsic sample can fall and be immersed in the liquid contained in said lower chamber of the container.

BRIEF DESCRIPTION OF THE DRAWINGS

Additional features of the invention will appear clear from the detailed description below, which refers to merely illustrative, not limiting embodiments, as illustrated in the attached drawings, wherein.

DETAILED DESCRIPTION OF PREFERRED EMBODIMENTS OF THE INVENTION

Figure 1:
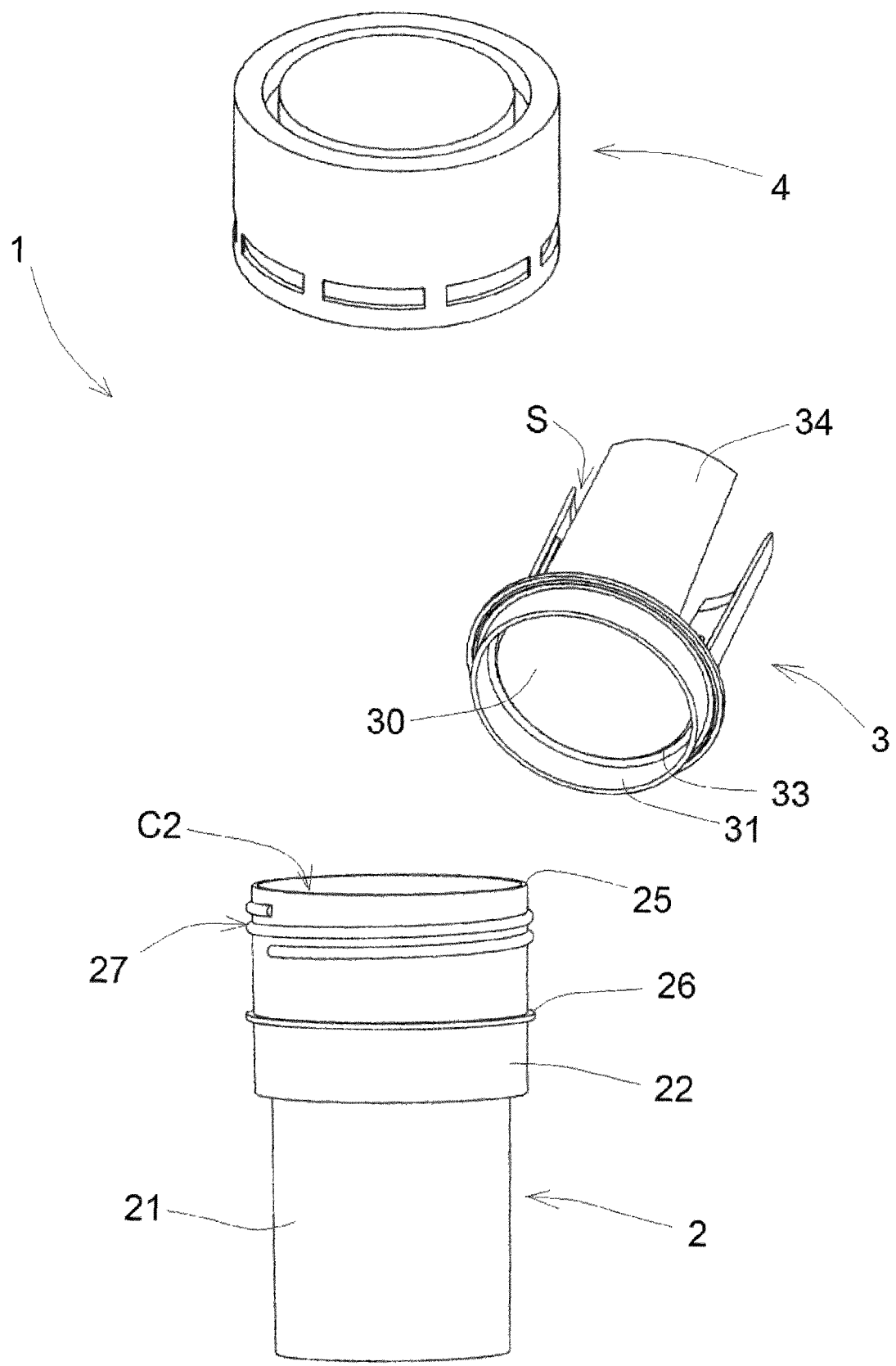
FIG. 1 is an exploded perspective view of the container assembly for biopsy according to a first embodiment of the invention.

With reference to FIGS. 1 to 13, the container assembly according to the first embodiment of the invention is described, which is generally indicated with reference numeral 1.

Now with reference to FIG. 1, the assembly (1) comprises:
a container (2),
a partition (3) mounted inside the container (2), and
a cover (4) that can be applied onto the container (2).

Figure 2:
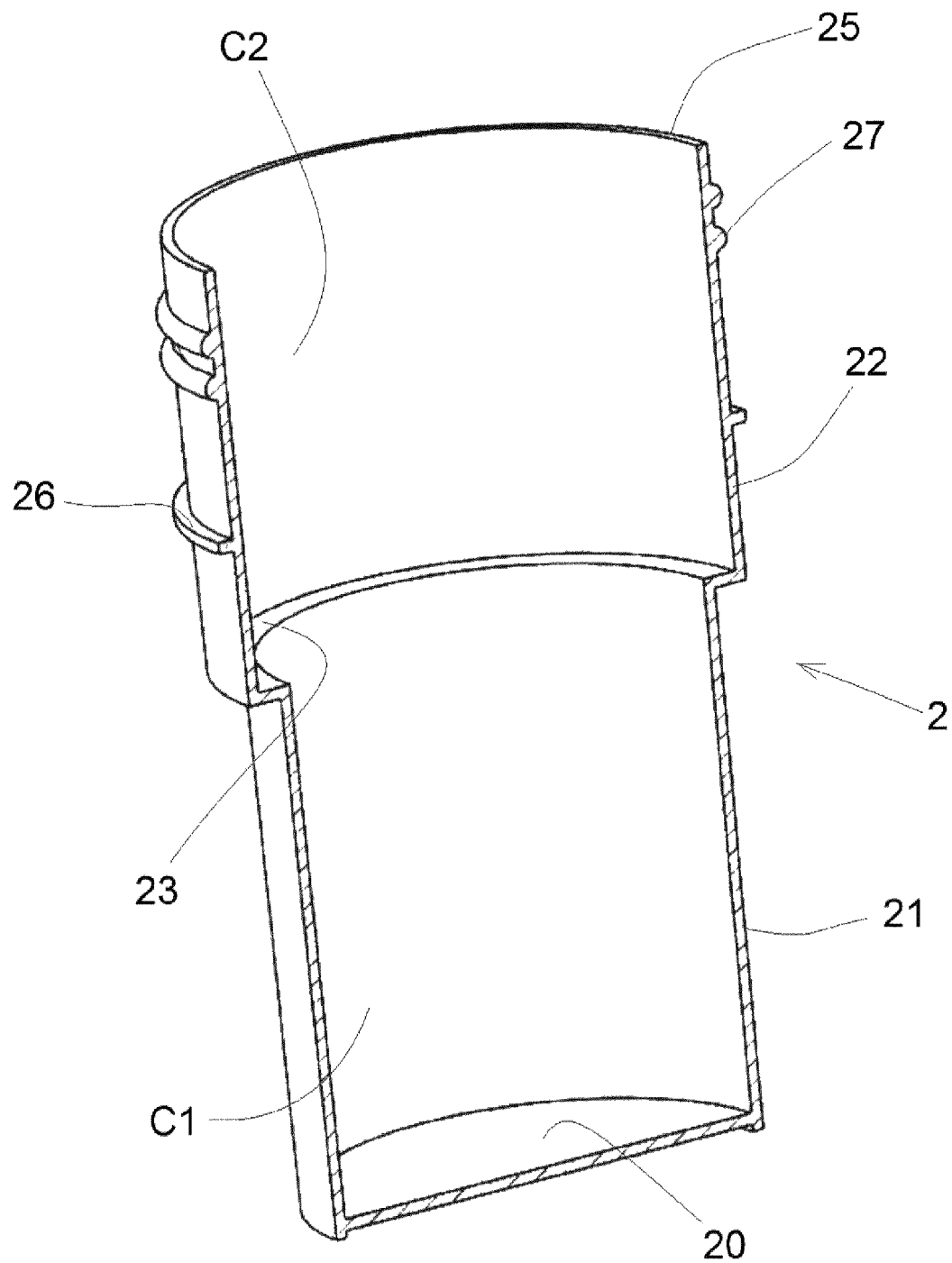
FIG. 2 is an axial perspective view of a container of the assembly of FIG. 1.

With reference to FIG. 2, the container (2) has a basically cylindrical shape, is internally empty and open on top.

The container (2) has a bottom wall (20) and a lower lateral wall (21) that defines a lower chamber (C1). The lower lateral wall (21) is joined to an upper lateral wall (22) by means of a joining collar (23) that is shaped as a step projecting outwards form the lower wall (21). The upper lateral wall (22) ends with an upper edge (25). The upper lateral wall (22) forms an upper chamber (C2) that is open outwards and in communication with the lower chamber (C1).

The upper chamber (C2) has a higher diameter than the lower chamber (C1). The upper chamber (C2) has a lower height than the lower chamber (C1). The lower chamber (C1) has a higher volume than the upper chamber (C2).

The lower chamber (C1) is intended to be completely filled with a liquid (L) (FIG. 9), such as for example formaldehyde or the like, intended to preserve biopsic samples.

The upper lateral wall (22) has a collar (26) that projects outwards, disposed at approximately half of the height of the upper lateral wall.

The upper lateral wall (22) has an external thread (27) disposed in the proximity of the upper edge (25).

The container (2) is made of a rigid plastic material, such as for example polypropylene, by means of injection molding, and is preferably made in one piece.

Figure 3:
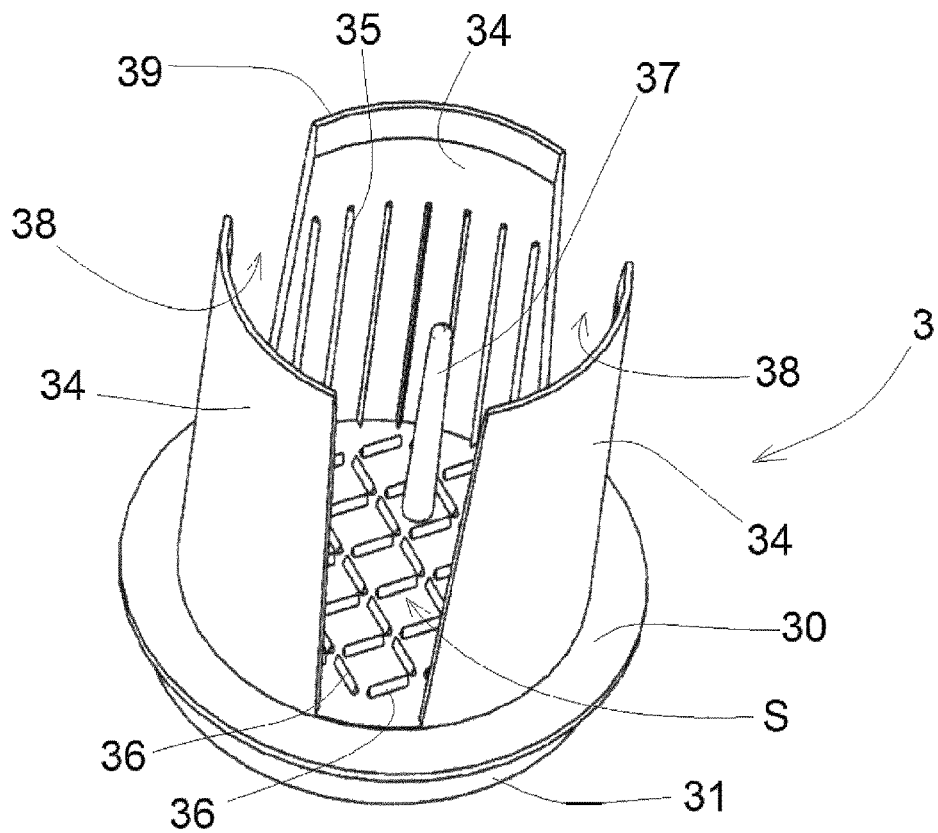
FIG. 3 is a perspective view of a partition of the assembly of FIG. 1.
Figure 4:
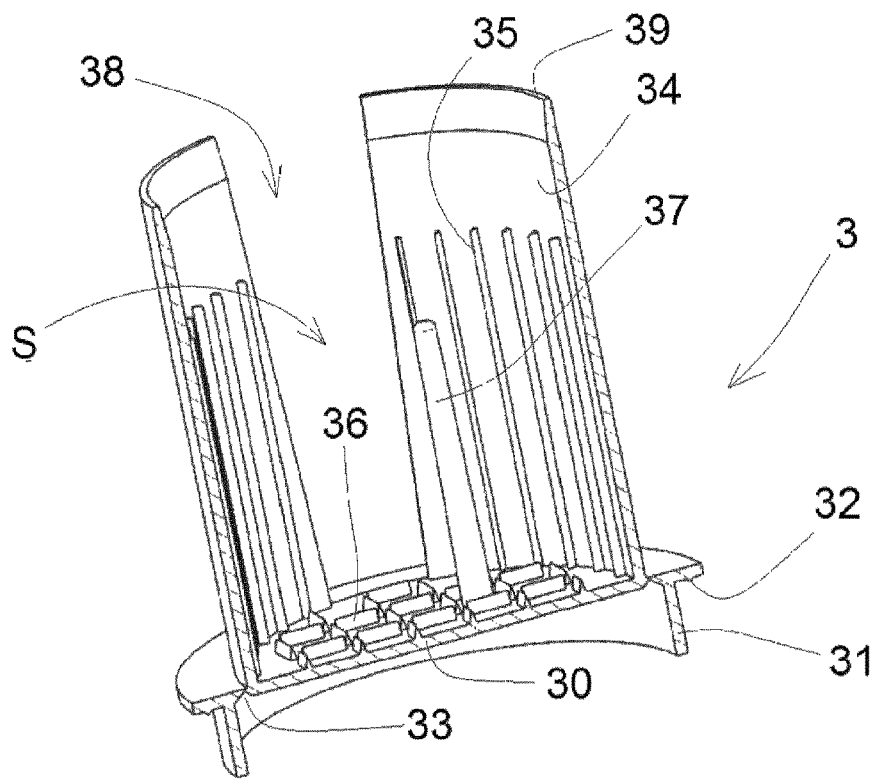
FIG. 4 is an axial perspective view of the partition of FIG. 2.

With reference to FIGS. 3 and 4, the partition (3) comprises a base wall (30) with disc-like shape. The base wall (30) has a lower diameter than the upper chamber (C2) of the container. The base wall (30) has a higher diameter than the lower chamber (C2) of the container. In view of the above, the base wall (30) of the partition is inserted in the upper chamber (C2) of the container and is stopped against the joining collar (23) of the container.

The partition (3) comprises a lower lateral wall (31) with cylindrical shape that extends in lower position from the base wall. The lower lateral wall (31) of the partition has an external diameter that is slightly lower than the diameter of the lower chamber (C1) of the container, in such a way that the lower lateral wall (31) of the partition enters the lower chamber (C1) of the container, centering the base wall (30) of the partition on the joining collar (23) of the container.

An annular rib (32) projects in lower position from the base wall (30) of the partition, in peripheral position with respect to the lower lateral wall (31). The annular rib (32) of the partition is stopped against the joining collar of the container. Such a rib (32) is used for ultrasonic welding in order to ensure a fluid-tight seal of the lower chamber (C1) of the container.

A lateral wall (34) raises from the base wall (30) in such manner to define a compartment (S) intended to receive one or more biopsic samples.

The lateral wall (34) can be discontinuous with elements shaped as cylindrical portions that are mutually separated by openings (38). The lateral wall (34) is disposed on the base wall (30) along a circumference having a slightly lower diameter than the lower lateral wall (31).

Disengageable connection means connect the base wall (30) of the partition to the container (2) in a disengageable way. In the container assembly (1) according to the first embodiment, the disengageable connection means comprise an weakening annular groove (33) obtained in the base wall (30) that generates a thinning of the thickness of the base wall and therefore an invitation to break the base wall along the weakening groove (33). The weakening groove (33) is obtained in the lower surface of the base wall (30), in a space comprised between the circumference of the upper lateral walls (34) and the circumference of the lower lateral wall (31) of the partition. The weakening annular groove (33) of the base wall is disposed in peripheral position with respect to the upper lateral walls (34) of the partition.

The lateral wall (34) of the partition has an upper edge (39). The lateral wall (34) of the partition has a slightly higher height than the upper lateral wall (22) of the container. The lateral wall (34) of the partition has a tapered upper portion with decreasing thickness going towards the upper edge (39).

The lateral wall (34) of the partition has a plurality of inwards-facing parallel longitudinal ribs (35).

A plurality of projections (36) with triangular shape is disposed on the base wall (30) of the partition, inside the circumference defined by the lateral wall (34). The projections (36) are arranged as the sides of a square.

Figure 4A:
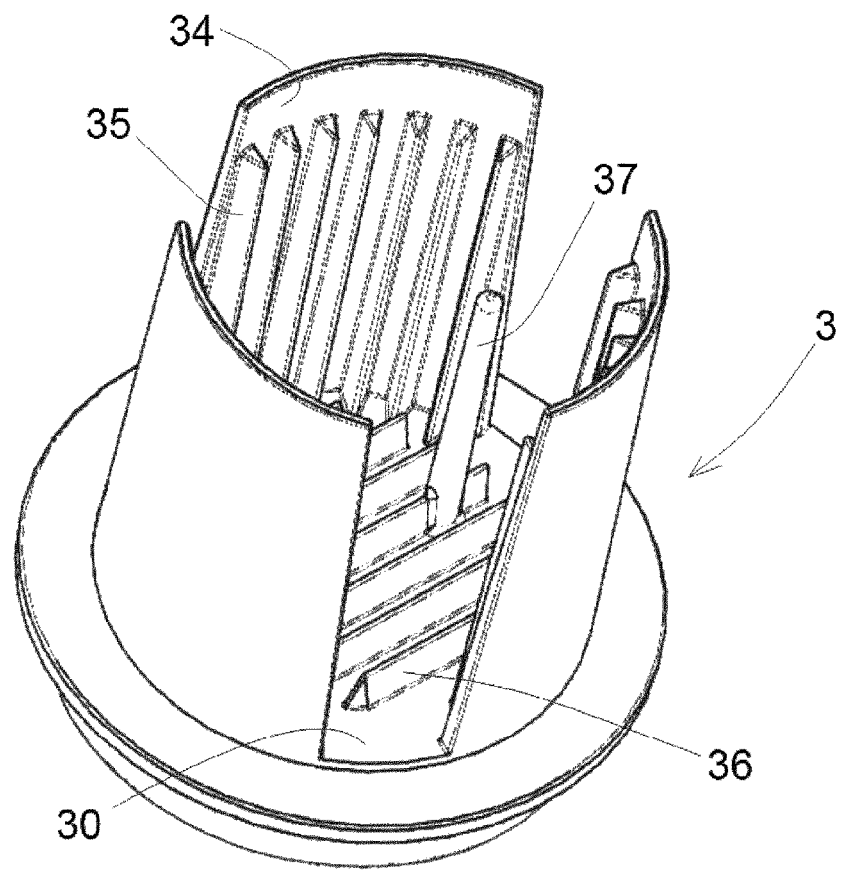
FIGS. 4A and 4B are the same views as FIGS. 3, 4 that show a variant of the partition.
Figure 4B:
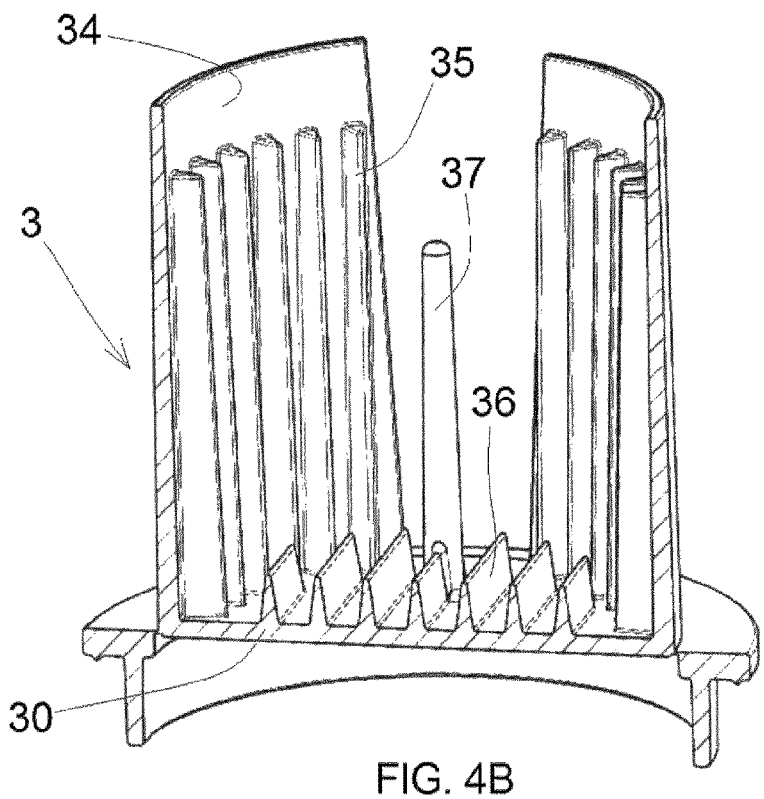

With reference to FIGS. 4A and 4B, the projections (36) can be triangular ribs disposed in parallel position and spaced by a distance that is substantially equal to the width of the base of the rib.

The longitudinal ribs (35) and the projections (36) of the partition are intended to generate a counter-surface to facilitate the detachment of the biopsic from the surgical instrument that is used to take the sample, as well as to prevent the biopsic sample from adhering to the base wall (30) or to the lateral wall (34) of the partition.

Advantageously, a pin (37) raises from the base wall (30) inside the space (S) defined by the lateral wall (34) of the partition. The pin (37) is disposed in eccentric position and is intended to detach the biopsic sample from the surgical instrument.

The partition (3) is made of rigid plastic material, such as for example polypropylene filled with calcium carbonate, by means of injection molding, and is preferably made in one piece. For this reason, a sufficiently rigid plastic material with specific weight of about 1.25 has been chosen, i.e. with a specific weight higher than the specific weight of the preservation liquid, in such a way that (after being broken, as explained hereinafter) the partition (3) can be easily immersed in the preservation liquid contained in the lower chamber (C1) of the container.

Figure 5:
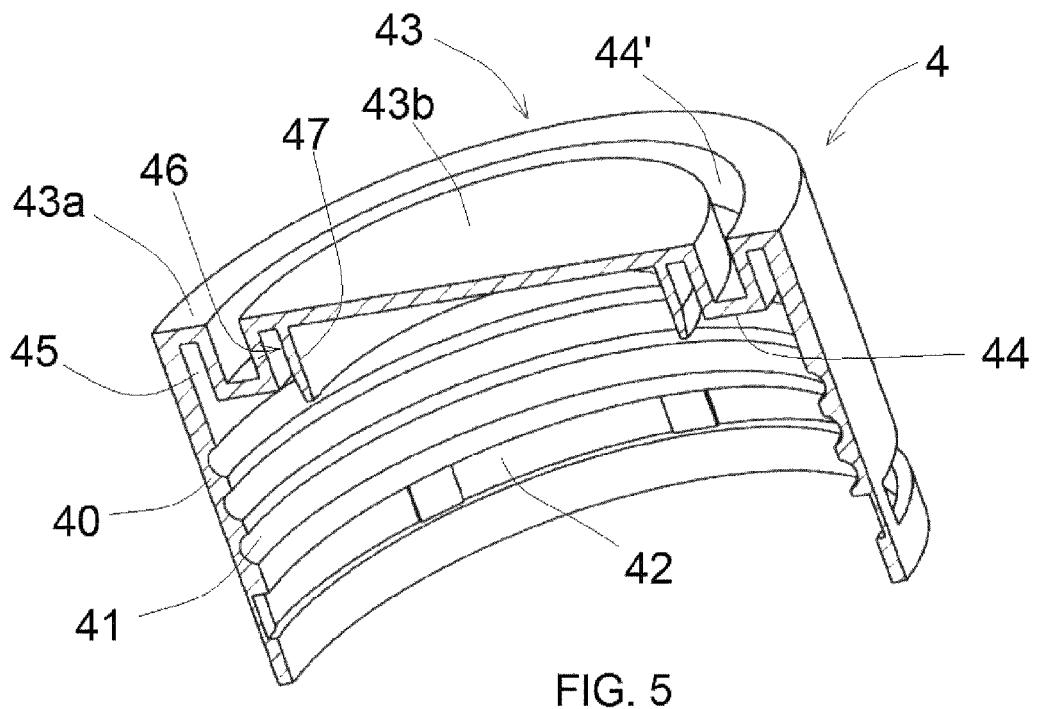
FIG. 5 is an axial perspective view of a cover of the assembly of FIG. 1.
Figure 6:
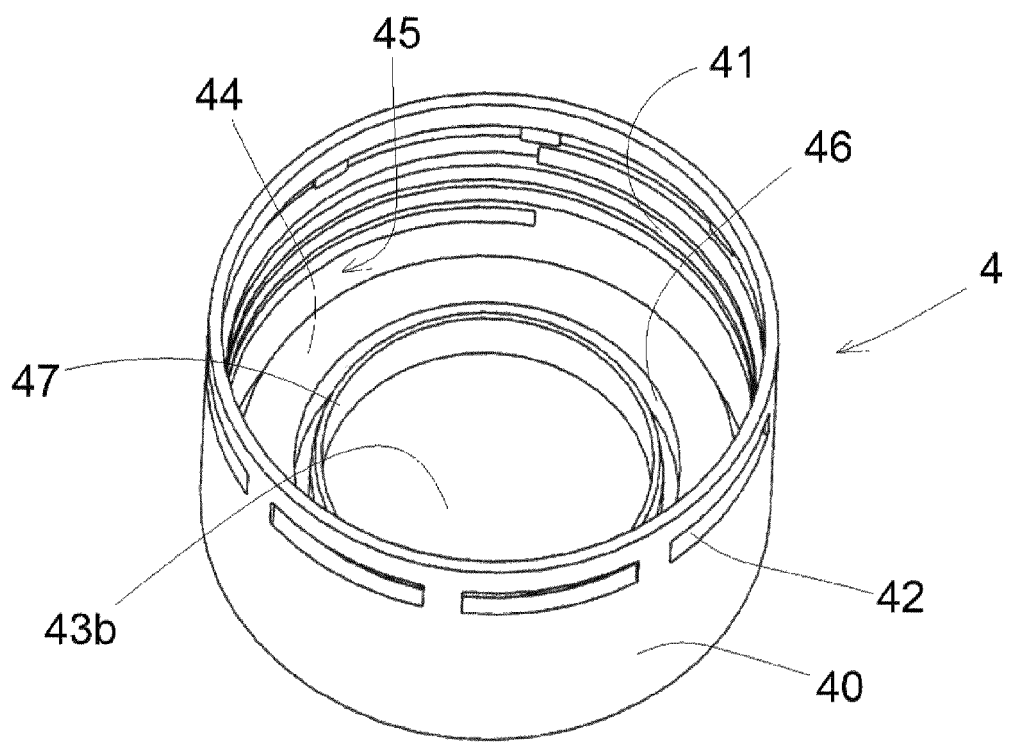
FIG. 6 is a perspective view of the cover of FIG. 5.

With reference to FIGS. 5 and 6, the cover (4) has a substantially cylindrical shape and is opened on the bottom. The cover has a lateral wall (40) joined to an upper wall (43). The lateral wall has a bottom edge (29). See FIG. 7.

The lateral wall (40) of the cover has an internal thread (41) that is intended to be screwed onto the external thread (27) of the container.

Openings (42) are obtained in the lateral wall (40) of the cover under the internal thread (41). The openings (42) are intended to receive an anti tampering strap (A) (FIG. 9) of known type, which is therefore not illustrated in detail. Initially, the cover (4) is screwed onto the container (2) and the anti-tampering strap (A) prevents the cover from moving with respect to the container. The anti-tampering strap (A) is automatically broken when the cover is screwed onto the container. Alternatively, the anti-tampering strap (A) can be manually removed by the user, in such a way to let the cover move with respect to the container.

The upper wall (43) of the cover is provided with a peripheral portion (43*a*) joined to a disc-like central portion (43*b*) by means of an annular joining rib (44) that protrudes in lower position. The annular joining rib (44) can be lightened by an upward-facing annular lightening rib (44').

A first annular rib (45) is formed between the lateral wall (40) and the annular joining rib (44).

Guide means (47) guide the cover (4) on the lateral wall (34) of the partition. The guide means (47) comprise an annular guide rib that protrudes in lower position from the central portion (43*b*) of the upper wall of the cover. The annular guide rib has a tapered ending portion with decreasing thickness going towards the ending edge of the annular guide rib.

An annular guide groove (46) is formed between the annular joining rib (44) and the annular guide rib (47).

Figure 7:
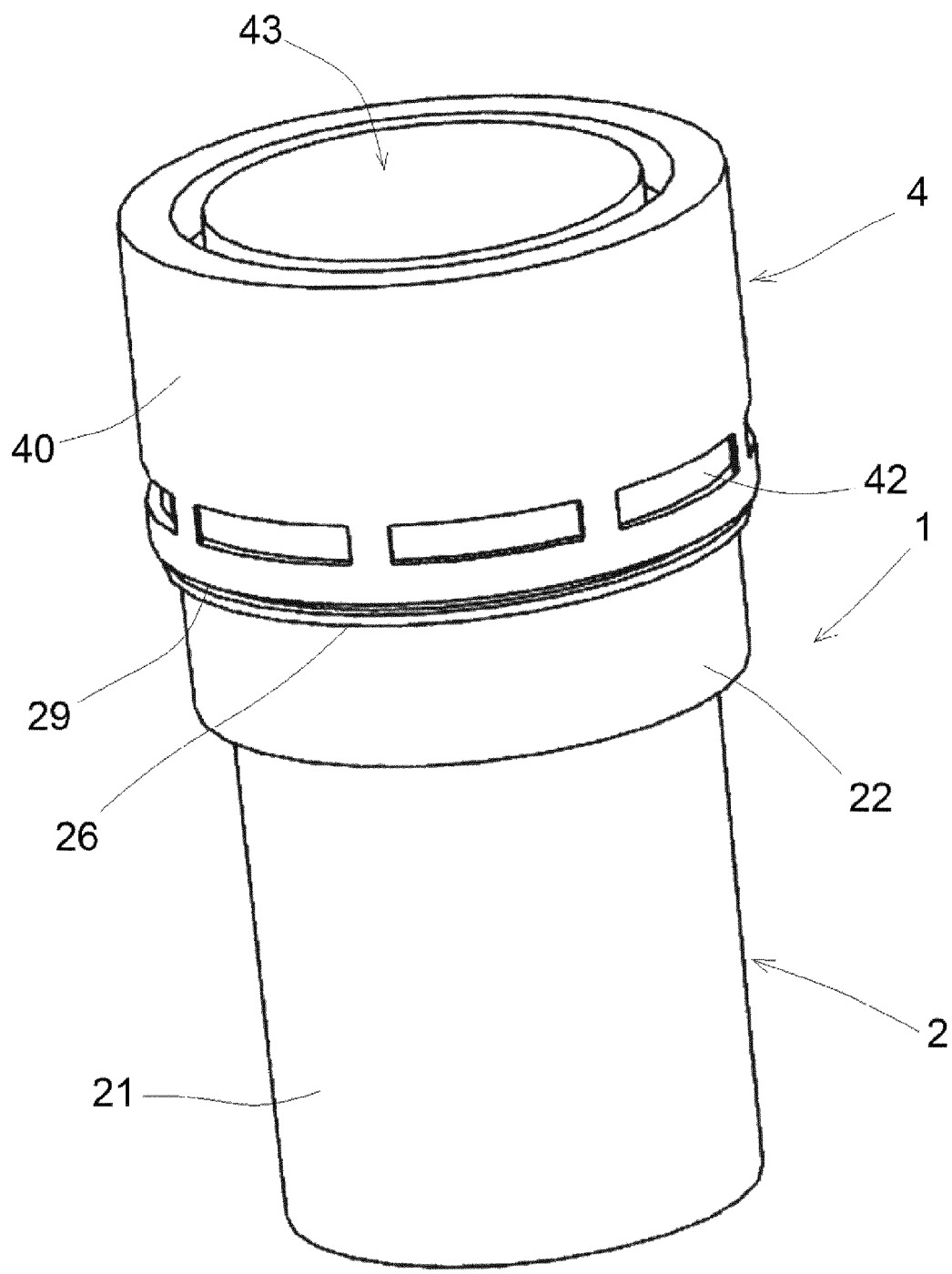
FIG. 7 is a perspective view of the container assembly of FIG. 1 in assembled condition.
Figure 8:
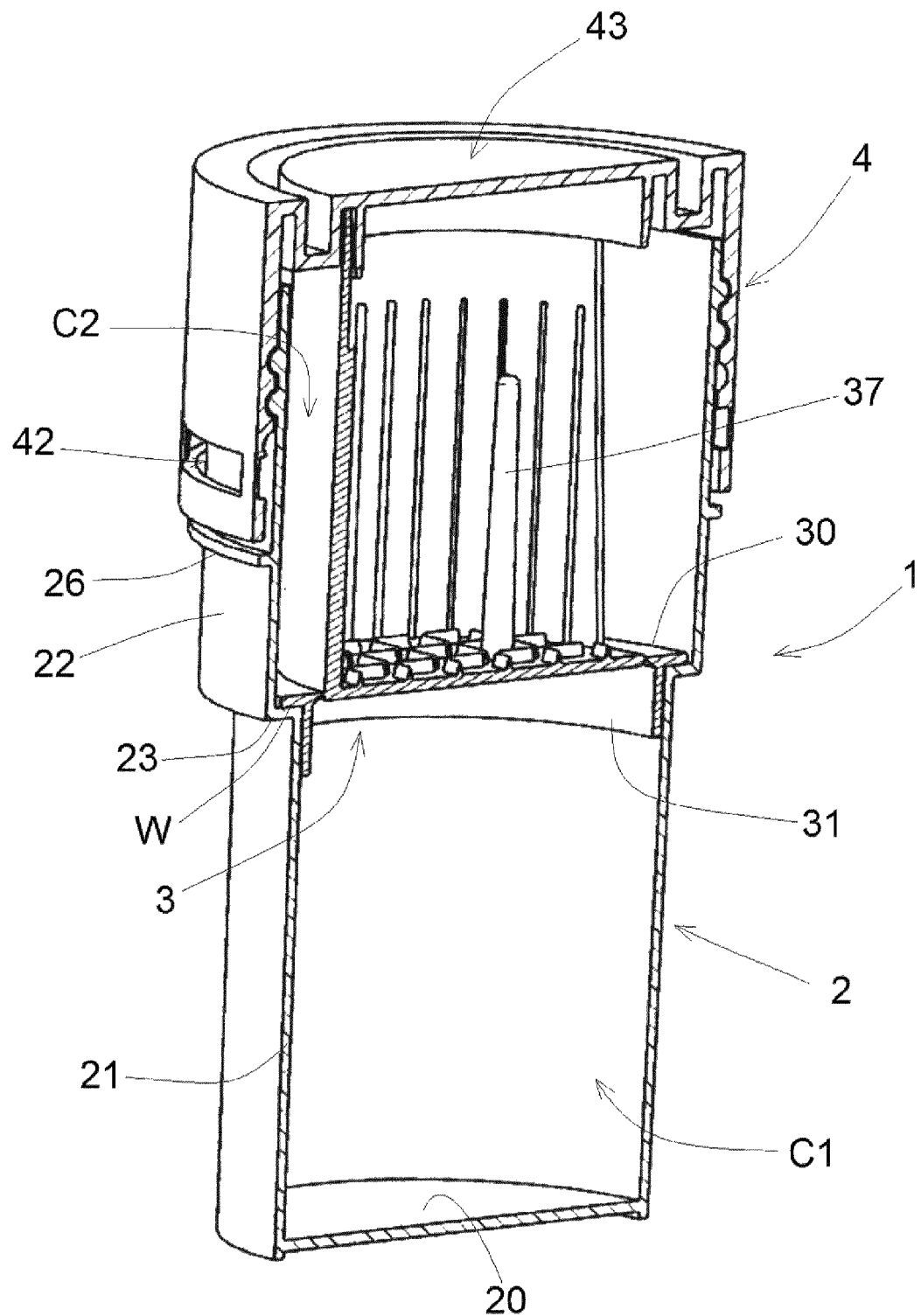
FIG. 8 is an axial perspective view of the assembly of FIG. 7 in assembled condition.

The cover (3) is made of rigid plastic material, such as for example polypropylene, by means of injection molding, preferably in one piece. FIGS. 7 and 8 show the container assembly (1) in assembled condition, wherein the preservation liquid and the anti-tampering strap (A) are not shown.

The lower chamber (C1) of the container is filled with a preservation liquid (L) (FIG. 9) and the partition (3) is inserted into the upper chamber (C2) of the container, in such a way that the annular rib (32) of the base wall (30) of the partition is stopped against the joining collar (23) of the container.

Now ultrasonic welding is made with a sonotrode that is operated along the circumference of the joining collar (23), in such a way that the annular rib (32) of the partition is melted, obtaining an annular welding line (W) (FIG. 9) that fixes in fluid-tight mode the base wall (30) of the partition on the joining collar (25) of the container.

The cover (4) is screwed onto the container (2), in such a way to cover the partition (3) and an anti-tampering strap (A) (FIG. 9) is applied to the cover (4) to prevent the cover from moving with respect to the container.

Figure 8A:
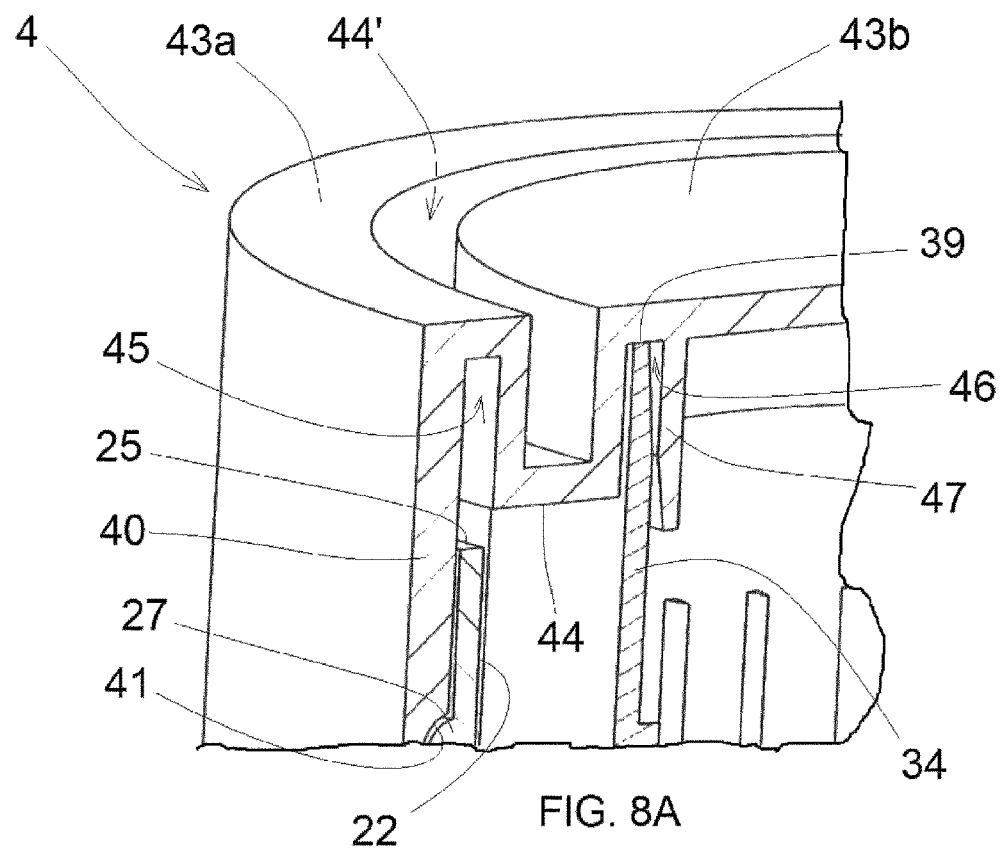
FIGS. 8A and 8B are two enlarged details of FIG. 8.
Figure 8B:
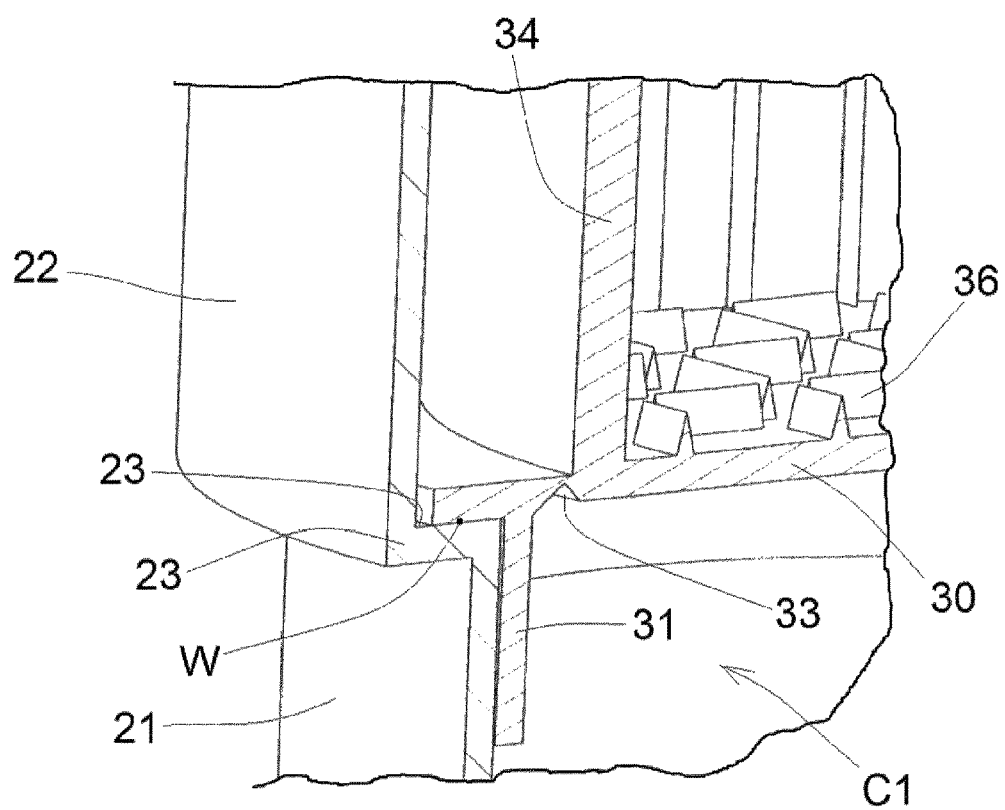

As shown in FIG. 8A, the internal thread (41) of the cover is screwed onto the external thread (27) of the container. The upper part of the lateral wall (34) of the partition is engaged inside the annular guide groove (46) of the cover. The upper edge (39) of the upper lateral walls (34) of the partition is in contact with the central portion (43*b*) of the upper wall of the cover.

The upper edge (25) of the container is disposed in register under the first annular groove (45) of the cover.

Figure 9:
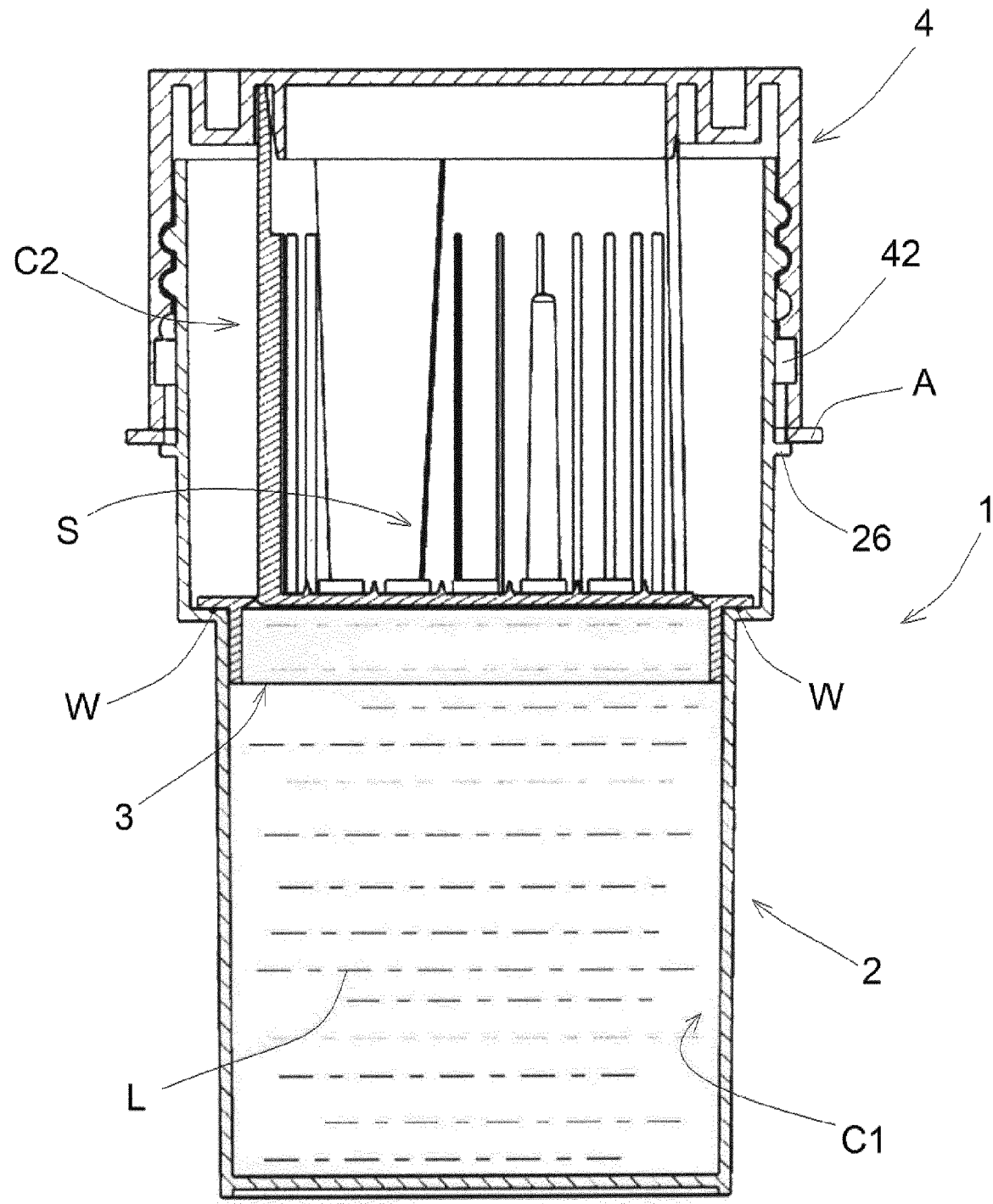
FIGS. 9-13 are axial views of the container assembly according to the first embodiment of the invention during different steps.

With reference to FIG. 9, a preservation liquid (L) is initially disposed in the lower chamber (C1) of the container and the anti-tampering strap (A) is mounted in the cover, cooperating with the collar (26) of the container to prevent the cover (4) from moving with respect to the container (2). Now, in order to use the container assembly (1), the user screws the cover onto the container in order to break the anti-tampering strap (A).

Figure 10:
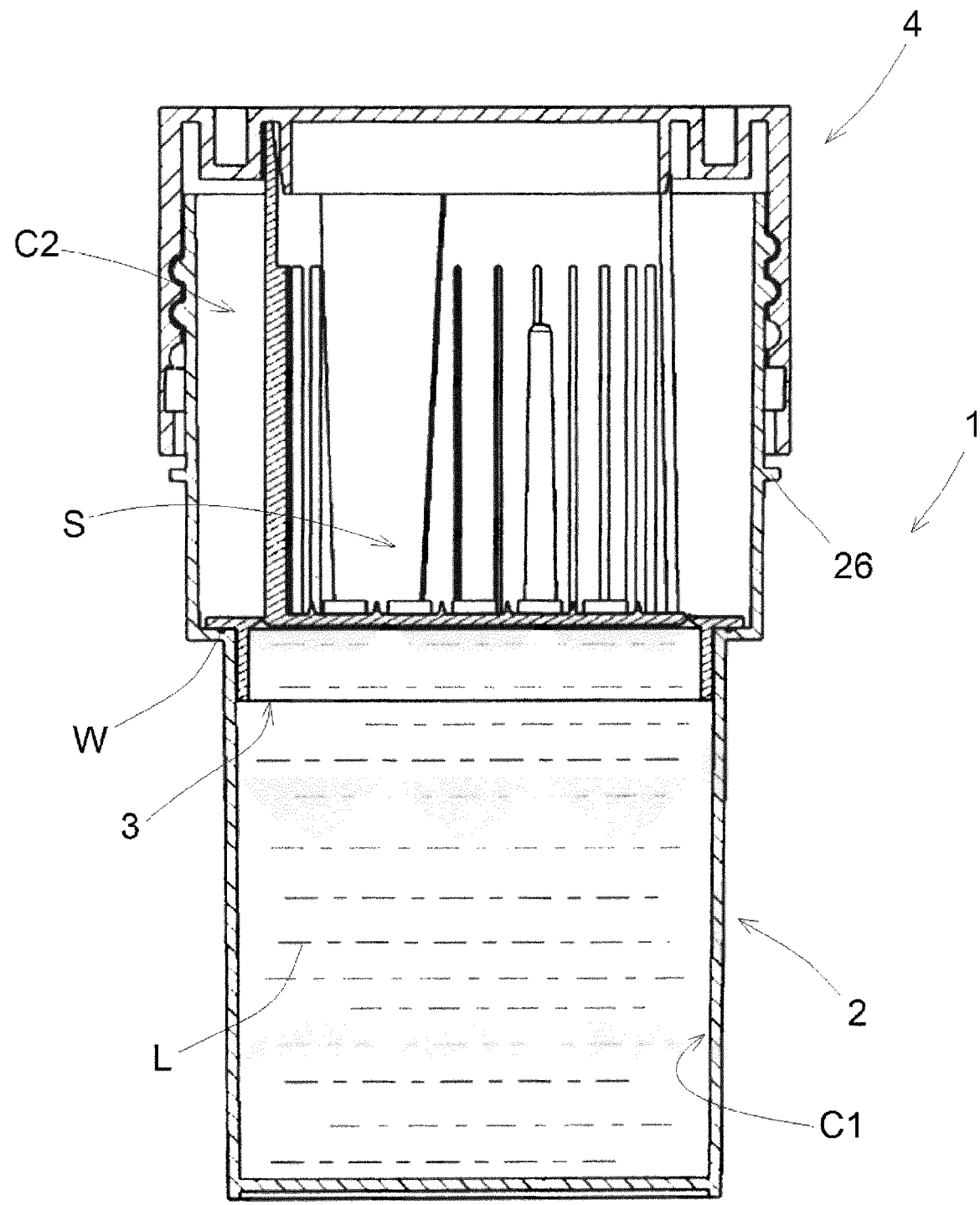

With reference to FIG. 10, the user has broken the anti-tampering strap (A). In this way, the cover (4) is no longer tied to the container.

Therefore, the cover can move with respect to the container and the user can unscrew the cover (4) in order to remove it from the container (2). The removal of the cover (4) does not cause the leakage of the liquid (L), which is closed in fluid-tight mode in the lower chamber (C1) of the container.

Figure 11:
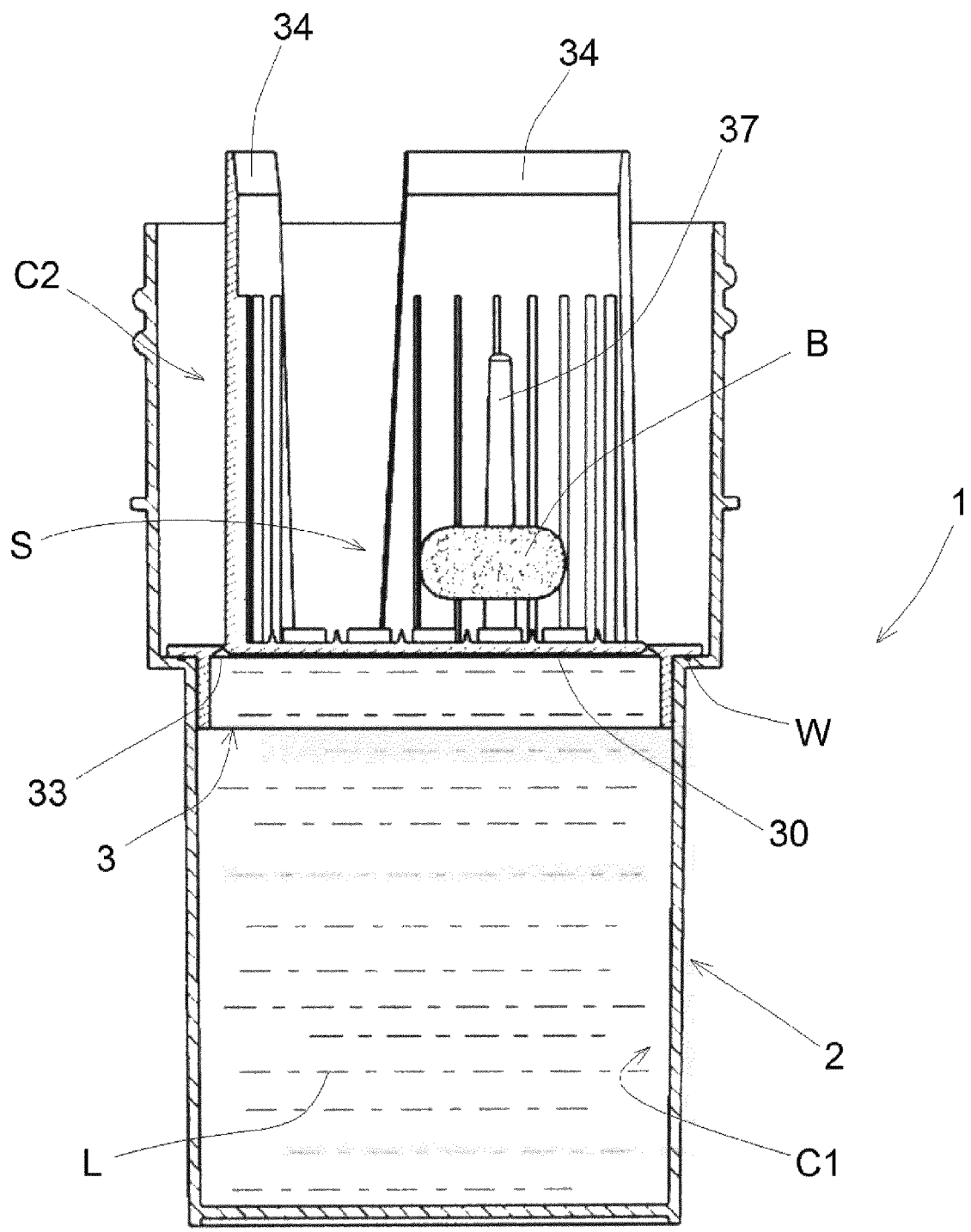

With reference to FIG. 11, the user has removed the cover (4) and has introduced a biopsic sample (B) in the compartment (S) defined by the base wall (30) and by the lateral wall (34) of the partition.

Figure 12:
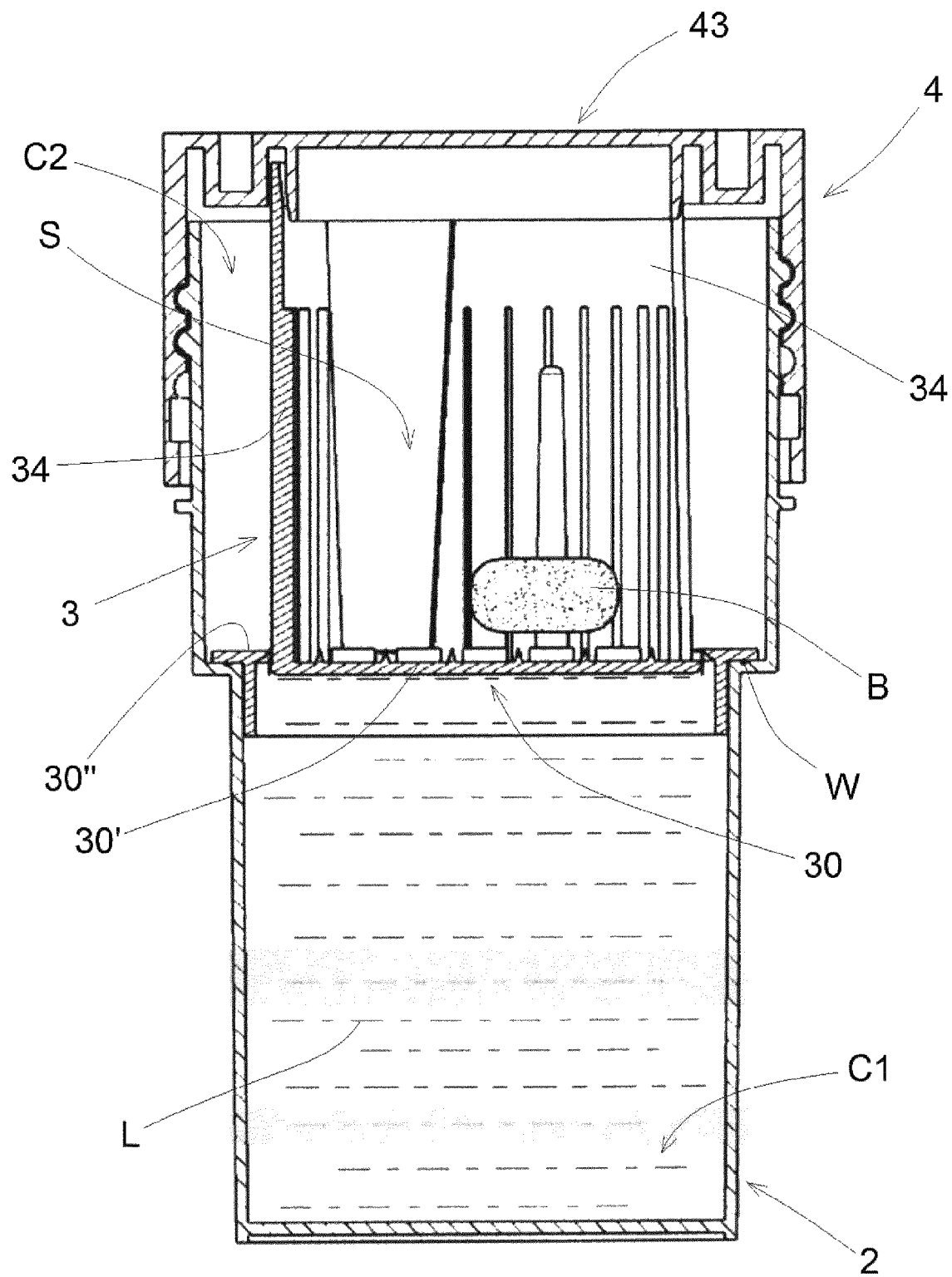

With reference to FIG. 12, the user screws the cover (4) onto the container. Consequently, the upper wall (43) of the cover is stopped against the upper edge (39) of the lateral wall of the partition, pushing the partition downwards.

Considering that the peripheral part of the base wall (30) of the partition is welded to the joining collar (23) of the container, the base wall (30) of the partition is broken along the annular weakening groove (33) and a central part (30') of the base wall (30) of the partition is detached from a peripheral portion (30") of the partition.

The central part (30') of the base wall of the partition is connected to the upper lateral wall (34) that defines the compartment (S) wherein the biopsic sample (B) is disposed.

Figure 13:
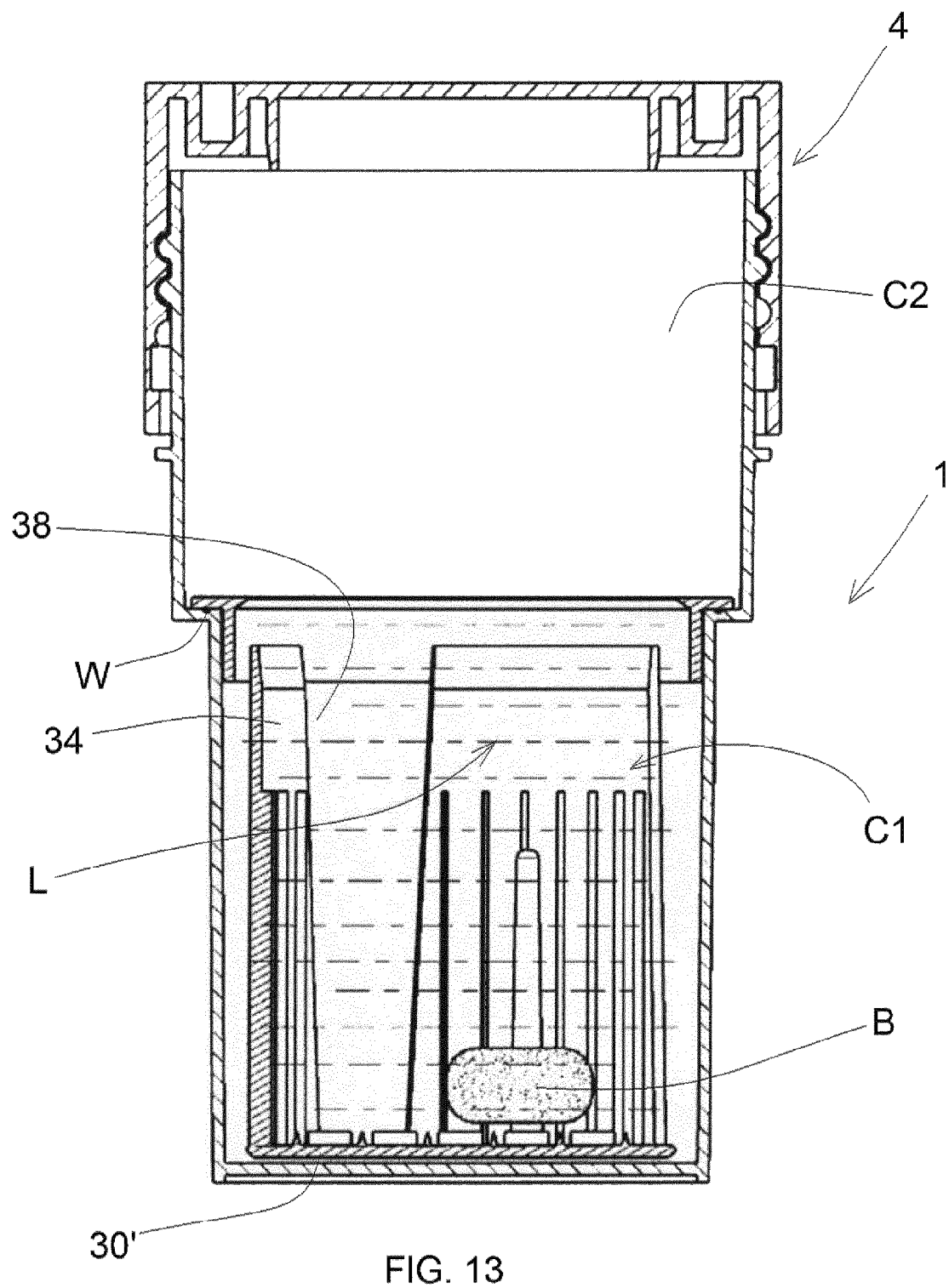
Figure 14:
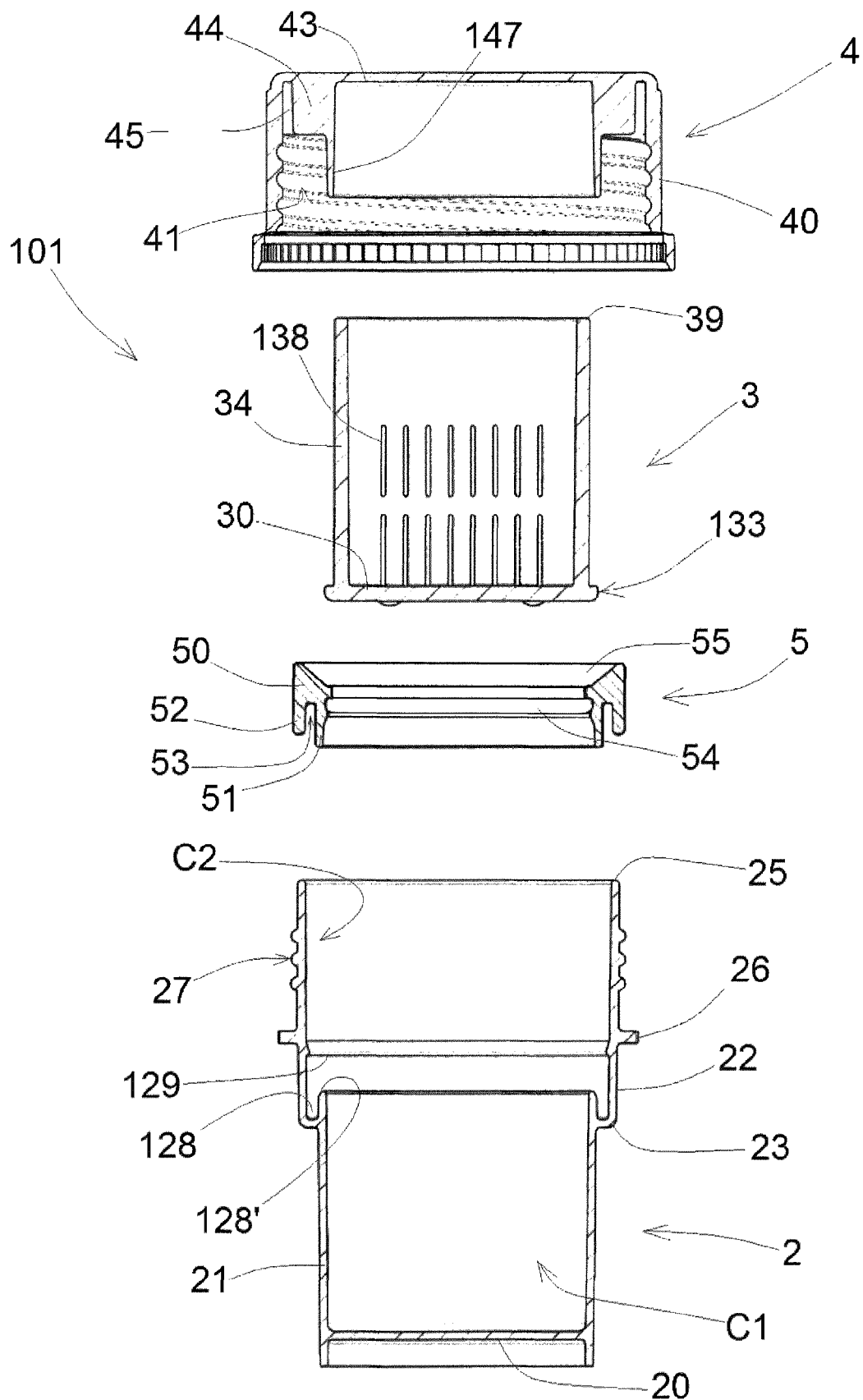
FIG. 14 is an exploded view of a container assembly according to a second embodiment of the invention.
Figure 15:
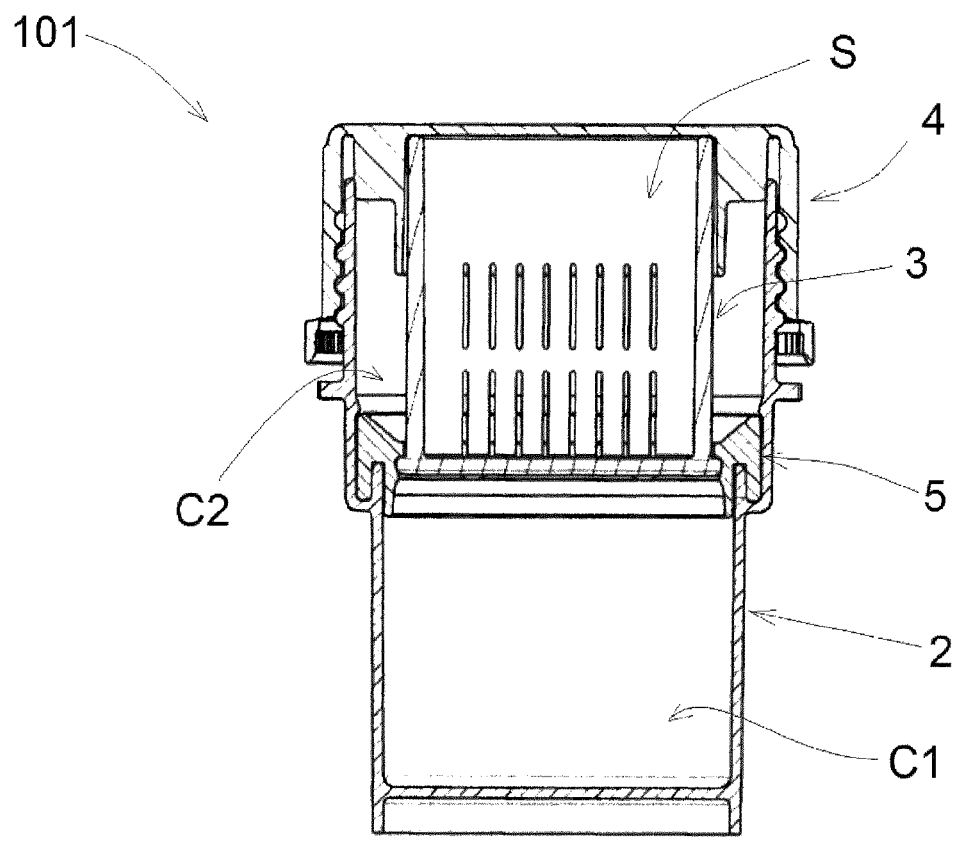
FIG. 15 is a sectional view of the container assembly of FIG. 14 in assembled conditions.
Figure 15A:
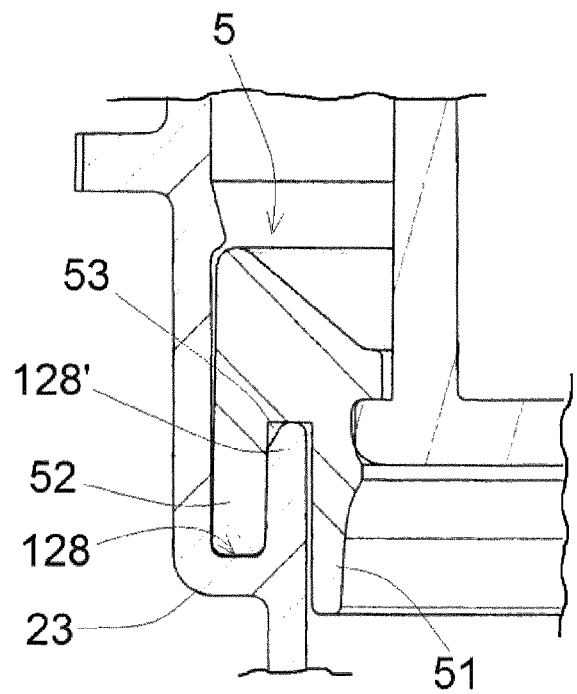
FIG. 15A in an enlarged detail of FIG. 15.
Figure 16:
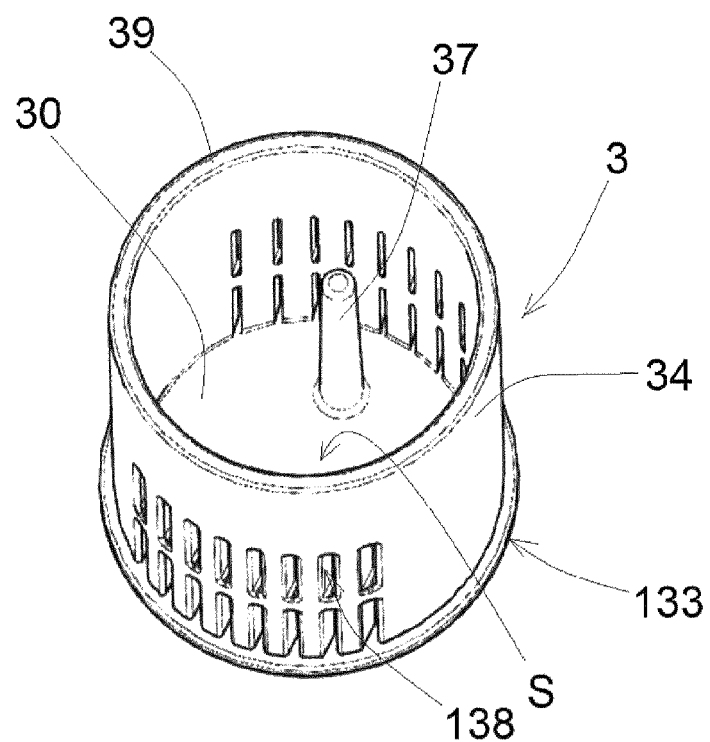
FIG. 16 is a perspective view of the partition of the container assembly of FIG. 15.
Figure 17:
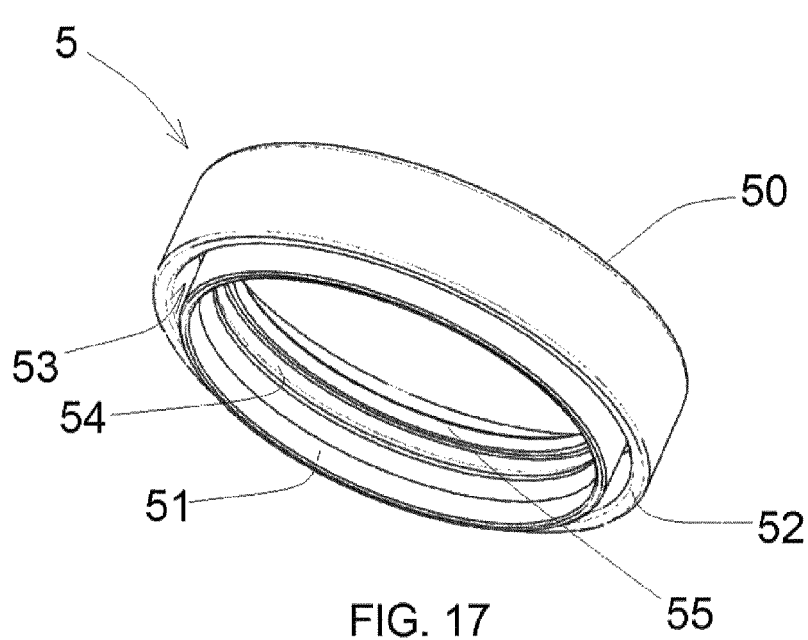
FIG. 17 is a perspective view of the seal of the container assembly of FIG. 15.

With reference to FIG. 13, the central part (30') of the base wall of the partition falls into the liquid (L) inside the lower chamber (C1) of the container. The liquid (L) passes through the openings (38) between the lateral wall (34) of the partition and filters onto the central part (30') of the base wall of the partition, causing the drowning of the partition with the biopsic sample (B). Consequently, the biopsic sample (B) is totally immersed in the liquid (L). The cover (4) guarantees the hermetic closing of the container assembly (1).

Even if the container assembly (1) is overturned and the liquid (L) goes to the upper chamber (C2), the central part (30') of the base wall of the partition is in any case drowned in the liquid (L), thus guaranteeing the total immersion of the biopsic sample (B).

In the following description the parts that are identical or correspond to the parts described above are identified with the same numerals, omitting their detailed description.

FIGS. 14 to 19 show a second embodiment of the container assembly, which is generally indicated with reference numeral 101.

In such a case, a housing (128) is obtained in the joining collar (23) of the container, said housing (128) being provided with an upward-projecting annular rib (128').

A collar (129) projects towards the interior of the upper lateral wall (22) of the container, being disposed above the housing (128).

Disengageable connection means connect the base wall (30) of the partition to the container (2) in an disengageable way.

According to this second embodiment, the disengageable connection means comprise a seal (5) housed in the housing (128) of the container. The seal (5) has an annular shape. Advantageously, the seal (5) is of double lip type. The seal (5) comprises a body (50) from which an internal lip (51) and an external lip (52) protrude, being separated by an annular groove (53). In such a way, the external lip (52) is engaged inside the housing (128) of the container and the annular rib (128') of the container is engaged inside the annular groove (53) of the seal.

An annular housing (54) is obtained on the internal surface of the internal lip (51) of the seal. The body (50) of the seal has a tapered surface (55) that extends toward the housing (54) of the seal.

The partition (3) has a disc-shaped base wall (30) without weakening groove. The base wall (30) has a perimeter edge (133) intended to be hermetically engaged in the housing (54) of the sale, in such a way to isolate the lower chamber (C1) from the upper chamber (C2) wherein the partition (3) is disposed.

The partition (3) has only one cylindrical lateral wall (34) wherein through slots (138) are obtained, which are intended to let the liquid pass through.

Evidently, the partition of the container assembly (101) of the second embodiment can be provided with the ribs (35, 36) shown in the partition of the container assembly (1) of the first embodiment.

The cover (4) comprises an annular joining rib (44) that protrudes in lower position from the upper wall (43) of the cover.

Guide means (147) have the shape of a cylindrical guide rib that protrudes in lower position from the joining rib (44) in order to be disposed in the lateral wall (34) of the partition in such a way to guide the cover when the partition is pushed.

Figure 18:
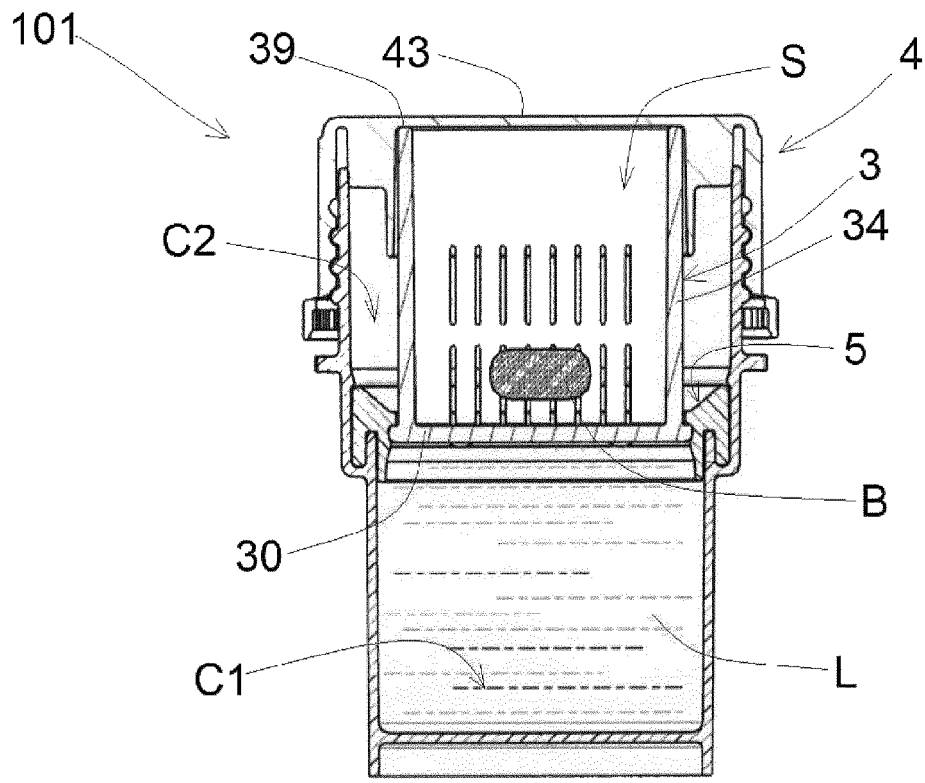
FIGS. 18 and 19 are axial views of the container assembly according to the second embodiment of the invention during different steps.

With reference to FIG. 18, the user has already introduced a biopsic sample (B) in the compartment (S) defined by the base wall (30) and by the lateral wall (34) of the partition.

The user screws the cover (4) onto the container. Consequently, the upper wall (43) of the cover is stopped against the upper edge (39) of the lateral wall of the partition, pushing the partition downwards.

Considering that the perimeter edge (133) of the base wall of the partition is engaged in the housing (54) of the seal, the seal is compressed and the perimeter edge (133) of the base wall of the partition is disengaged from the housing (54) of the seal.

Figure 19:
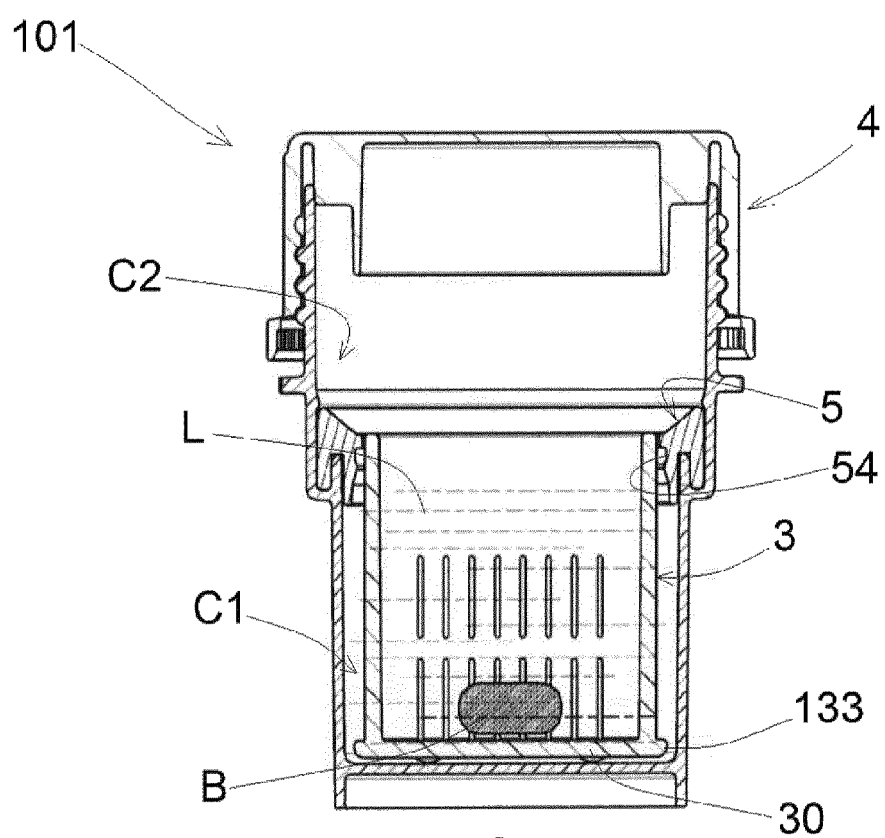

Consequently, as shown in FIG. 19, the partition falls by gravity into the liquid (L) contained in the lower chamber (C1) of the container. The liquid (L) penetrates through the through slots (138) of the lateral wall and the partition drowns into the liquid (L) contained in the lower chamber (C1) of the container.

Although two embodiments of the disengageable connection means are shown in the drawings, that is to say an annular weakening groove (33) obtained in the base wall of the partition and a seal (5) fixed to the container (2) and connected in an disengageable way to the partition, the invention can be provided with disengageable connection means of equivalent type, such as snap-in or adhesive couplings.

In any case, said disengageable connection means must provide:
- a connection between the partition (3) and the container (2) that ensures the fluid-tight seal between the lower chamber (C1) and the upper chamber (C2) of the container; and
- a disengagement of the partition (3) from the container (2) when the partition is pushed by the cover (4).

Numerous variations and modifications can be made to the present embodiments of the invention, which are within the reach of an expert of the field, falling in any case within the scope of the invention.

The invention claimed is:

1. A container assembly for biopsy comprising:
   a container including a lower chamber filled with a preservative liquid that preserves biopsic samples and an upper chamber disposed above the lower chamber,
   a partition disposed in the upper chamber of the container, the partition including a base wall connected to the container, in such a way to isolate the lower chamber from the upper chamber, the partition comprising a lateral wall that raises from the base wall to define a compartment for receiving a biopsic sample,
   a disengageable connector connecting the base wall of the partition to the container in a disengageable manner; and
   a cover that is coupled with the container and cooperates with the side wall of the partition in such manner to push the partition, to force the disengageable connector and to cause disengagement of a portion of the base wall of the partition from the container, such that the partition with the biopsic sample moves into the lower chamber and is immersed in the preservative liquid contained in the lower chamber;
   wherein the base wall includes an inner portion forming a bottom closure for the partition and an outer portion fixed to the container; and the disengageable connector comprises an annular weakening groove positioned on the base wall between the inner portion and the outer portion, the annular weakening groove being breakable as the cover pushes the partition into the lower chamber such that an entirety of the bottom closure is disengaged from the outer portion to move into the lower chamber.

2. The container assembly of claim 1, wherein the partition is made of rigid plastic having a specific weight that is higher than a specific weight of the preservative the liquid contained in the lower chamber.

3. The container assembly of claim 1, wherein a volume of the lower chamber is higher than a volume of the upper chamber.

4. The container assembly of claim 1, wherein the partition comprises ribs projecting from the lateral wall toward an interior of the partition for facilitating detachment of the biopsic sample from an instrument.

5. The container assembly of claim 1, wherein the partition comprises projections projecting from the base wall toward an interior of the partition for facilitating detachment of the biopsic sample from an instrument.

6. The container assembly of claim 1, wherein the partition comprises a pin projecting from the base wall toward an interior of the partition for facilitating detachment of the biopsic sample from an instrument.

7. The container assembly of claim 1, wherein the cover comprises an internal thread that is screwed onto an external thread of the container.

8. The container assembly of claim 1, and further comprising an anti-tampering strap that ties the cover to the container, the anti-tampering strap being breakable by screwing the cover or removable manually by a user.

9. The container assembly of claim 1, wherein the cover comprises:
- an upper wall configured for stopping against an upper edge of the lateral wall of the partition
- an annular groove for receiving an upper edge of the container and
- a guide surface for guiding sliding of the cover on the lateral wall of the partition.

10. The container assembly of claim 1, wherein the disengageable connector comprises a seal disposed in the container and provided with a seat configured to receive a perimeter edge of the base wall of the partition.

11. The container assembly of claim 10, wherein the seal includes an external lip that is engaged into a housing of the container and an internal lip including the seat for receiving the perimeter edge of the base wall of the partition.

12. The container assembly of claim 1, wherein the base wall of the partition and the container are connected by an ultrasonic weld.

13. The container assembly of claim 1, wherein the container comprises a joining collar disposed between the lower chamber and the upper chamber, the base wall of the partition being fixed to the joining collar of the container.

* * * * *